United States Patent
Sackner et al.

(10) Patent No.: US 6,413,225 B1
(45) Date of Patent: Jul. 2, 2002

(54) QUANTITATIVE CALIBRATION OF BREATHING MONITORS WITH TRANSDUCERS PLACED ON BOTH RIB CAGE AND ABDOMEN

(75) Inventors: Marvin A. Sackner, Miami Beach; D. Michael Inman, Miami, both of FL (US)

(73) Assignee: Vivometrics, Inc., Ventura, CA (US)

( * ) Notice: Subject to any disclaimer, the term of this patent is extended or adjusted under 35 U.S.C. 154(b) by 0 days.

(21) Appl. No.: 09/595,317

(22) Filed: Jun. 16, 2000

Related U.S. Application Data
(60) Provisional application No. 60/139,964, filed on Jun. 18, 1999.

(51) Int. Cl.$^7$ ................................................. A61B 5/00
(52) U.S. Cl. ........................ 600/529; 600/534; 600/538
(58) Field of Search ................................ 600/529–538; 128/897–898

(56) References Cited

U.S. PATENT DOCUMENTS

| | | | |
|---|---|---|---|
| 4,373,534 A | | 2/1983 | Watson ........................ 128/716 |
| 4,834,109 A | | 5/1989 | Watson ........................ 128/721 |
| 6,047,203 A | * | 4/2000 | Sackner et al. ......... 600/301 X |

* cited by examiner

*Primary Examiner*—Robert L. Nasser
(74) *Attorney, Agent, or Firm*—Pennie & Edmonds LLP

(57) ABSTRACT

A method for calibrating non-invasive breathing monitors with sensors placed on the rib-cage and abdomen of a subject includes determining an initial scaling factor and an optimal multiplicative factor for the readings of the rib-cage and abdomen sensors using one of a least squares, linear regression, or multi-linear regression techniques. A current scaling factor is determined on a periodic basis using qualitative device calibration techniques. The current scaling factor is used to monitor breathing and diagnose obstructive apneas. Furthermore, the optimal multiplicative and the current scaling factor are used to determine the current tidal volume.

5 Claims, 2 Drawing Sheets

QUANTITATIVE CALIBRATION OF BREATHING MONITORS WITH TRANSDUCERS PLACED ON BOTH RIB CAGE AND ABDOMEN

RELATED APPLICATIONS

This application claims priority from U.S. Provisional Patent Application Serial No. 60/139,964 which was filed on Jun. 18, 1999.

BACKGROUND OF THE INVENTION

1. Field of the Invention

The present invention related to a method for calibrating a breathing monitor which measures respiration volume by separately measuring and then summing the contributions from rib cage and abdomen plethysmograph sensors.

2. Description of the Related Art

A prior art procedure for calibrating breathing monitors with transducers placed on both the rib cage and abdomen is disclosed in U.S. Pat. No. 4,834,109, the entire contents of which is incorporated herein by reference. This procedure is referred to as Qualitative Device Calibration (QDC) and includes the step of determining a ratio (K), also referred to as the scaling factor, of the gains of the rib cage and abdominal transducers during natural breathing for reflecting the relative contributions of the rib cage and abdomen of a patient or subject to the respiration volume. During the calibration procedure, the tidal volume is made equal to the sum of the weighted rib-cage and abdomen waveforms during the calibration period and is designated as a baseline which is used to assess changes in tidal volume as a percent of the baseline. The tidal volume can be converted to an actual volume by breathing into a volume measurement device and obtaining a conversion factor designated as a multiplicative factor (M).

After the QDC procedure is completed, with or without the computation of M, the breathing monitor is capable of detecting obstructive apneas in which the upper airways become occluded while the subject makes respiratory efforts. Since the rib-cage and abdomen transducers are calibrated, the occlusion causes a flat or near flat sum of these two signals to be generated, indicating that there is no tidal volume. This condition may thus be diagnosed as an apnea or cessation of breathing.

Changes in breathing patterns of the subject and/or changes in the posture of the subject may affect the scaling factor K, causing shifts in the contributions of the rib-cage and abdomen to tidal volume and thereby causing inaccurate estimates of tidal volume. To counter this effect, the scaling factor of the gains K may be recomputed at different time intervals using the QDC procedure to ensure that the scaling factor matches current conditions. The multiplicative factor M, which corresponds to the initial calibration breathing pattern and posture, may also be affected by changes in posture and breathing patterns. Although the recalibration of M may also be accomplished, such recalibration requires that the subject periodically breath into an external measurement device. This somewhat conflicts with the purpose of the breathing monitor which is the long term, non-invasive respiratory monitoring.

Another prior art procedure for calibrating breathing monitors with transducers placed on both the rib cage and abdomen is disclosed in U.S. Pat. No. 4,373,534, the entire contents of which are expressly incorporated herein by reference. This reference discloses the least squares, linear regression, or multi-linear regression methods for calibrating respiratory inductive plethysmograph devices while simultaneously breathing into an external measurement device. At least two sets of rib-cage and abdomen measurements and breathing volume measurements are taken with each set having different ratios of rib-cage and abdomen contributions to tidal volume —i.e., different scaling factors. The two sets of readings or measurements are then used to determine the average scaling factor of the rib-cage and abdomen sensor gains and to determine the optimal multiplicative factor M. Since this method changes the rib-cage and abdomen contributions to tidal volume in each set of readings, this method yields an average value for both the scaling factor K and the multiplicative factor M. This method provides a better estimate of actual tidal volume during various postures and breathing patterns of the subject. However, it is more difficult to diagnose obstructive apneas using this method because this method uses average values and not actual values of the scaling factor K.

SUMMARY OF THE INVENTION

It is an object of the present invention to provide a calibration procedure for a non-invasive tidal volume measurement device which uses the two compartmental lung model which provides an accurate estimate of tidal volume without limiting the ability of the device to detect obstructive apneas.

A method for calibrating a non-invasive breathing monitor having a rib-cage sensor and an abdomen sensor according to an embodiment of the present invention, comprises the steps of determining an optimal multiplicative value for the rib-cage sensor and abdomen sensor readings via one of least squares, linear regression, and multi-linear regression techniques. A current scaling factor is then determined using a Qualitative Device Calibration procedure for the current posture and breathing pattern of the subject. The current scaling factor and readings from the rib cage and abdomen sensors are used to accurately diagnose obstructive apneas. The optimal multiplicative value, the current scaling factor, and readings from the rib cage and abdomen sensors are used to determine the current tidal volume.

The current scaling factor may be determined on a periodic basis based on a fixed time period or based on a moving window average related to a number of breaths.

The step of determining an optimal multiplicative value also includes determining a scaling factor which is used for determination of the multiplicative factor. At least two sets of readings of the rib-cage and abdoman sensors are taken, with each set having different ratios of rib-cage and abdomen contributions to the tidal volume. Therefore, the optimal multiplicative is an average multiplicative for the various sets of readings.

The scaling factor used for determining the optimal multiplicative may be used for diagnosing apneas, particularly if the subject has not changed positions or breathing patterns. However, in the preferred embodiment, the current scaling factor is used.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

Figure 1:
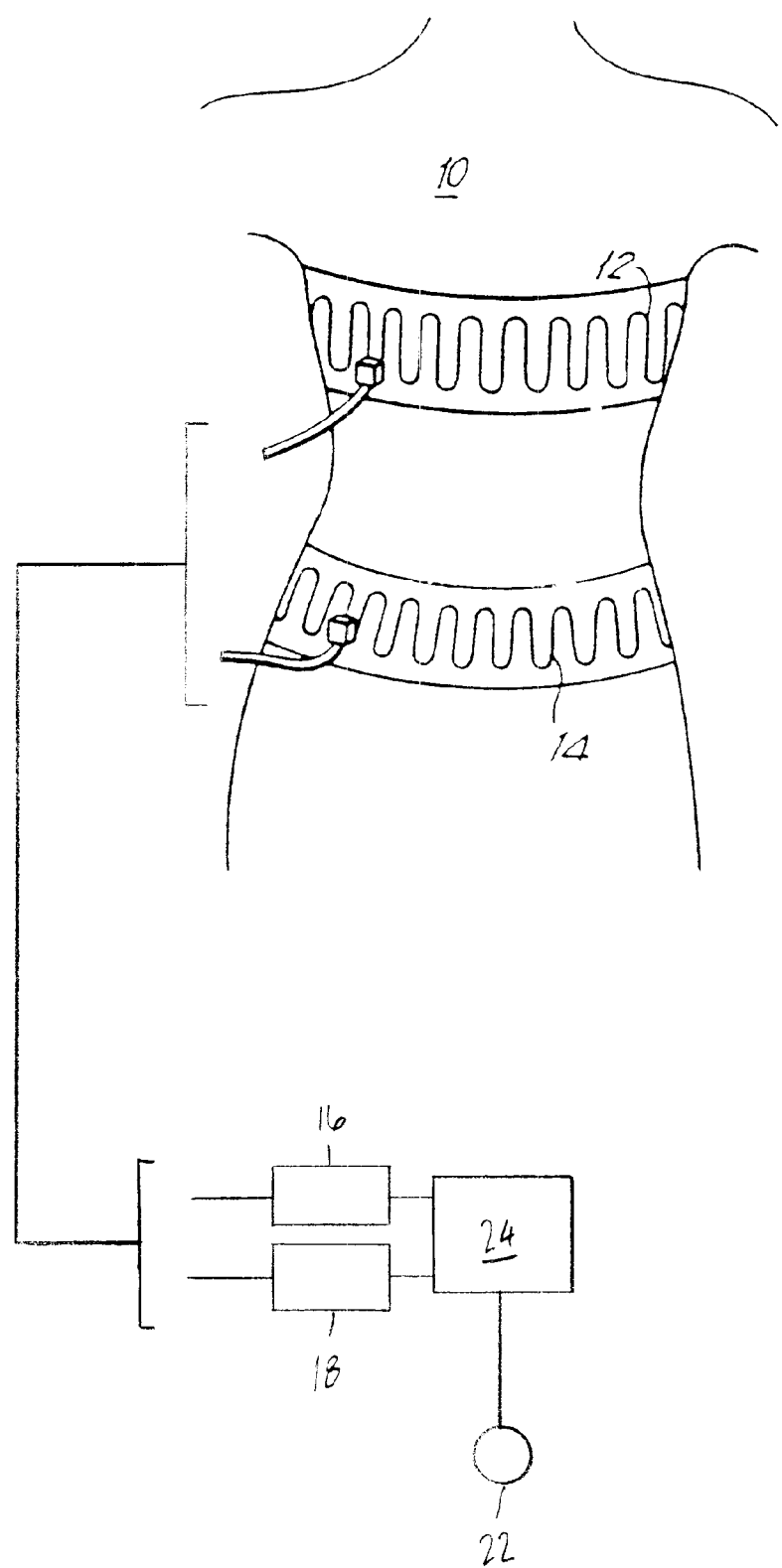
FIG. 1 is a schematic view showing a breathing monitor according to an embodiment of the present invention.
Figure 2:
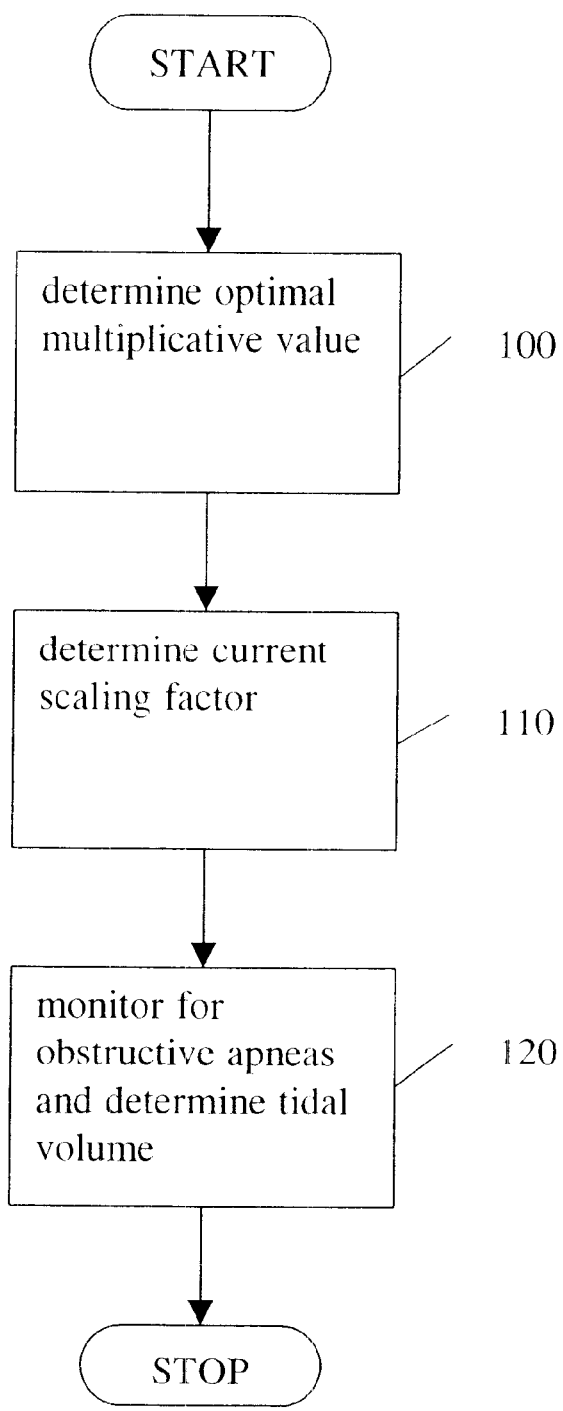
FIG. 2 is a flow diagram showing the steps for calibrating a breathing monitor which measures respiration volume by separately measuring and then summing the contributions from the rib cage and the abdomen according to an embodiment of the present invention.

Referring now to FIG. 1, a breathing monitor for measuring tidal volume during respiration is disclosed including two sensors 12, 14 arranged on a torso of a subject 10 so that the sensors 12, 14 measure the contraction and expansion of the ribcage and the abdomen. The breathing monitor is based on the two compartment lung model. That is, the basis for measuring breathing is an approximation that the respiratory system moves in two degrees of freedom of motion, wherein one compartment of the two compartment lung is the rib-cage and the other compartment is the abdomen. In a preferred embodiment of the present invention, the sensors 12, 14 comprise inductive plethysmographic transducers for measuring the excursions of the rib-cage and abdomen. However, instead of inductive plethysmograph transducers, the breathing monitor may include a jerkin plethysmograph, linear differential transformers, magnetometers, a bellows pneumograph, strain gauges, piezoelectric devices, impedance pneumographs, or inductance circumferential transformers. The sensors 12, 14 are connected to a controller 24 via scaling amplifiers 16, 18. Furthermore, an airway monitoring device 22 such as a spirometer is also connected to the controller 24 for measuring actual tidal volume.

According to an embodiment of the present invention, the first step in the calibration procedure of the breathing monitor comprises determining an optimal multiplicative value M, step 100, using one of the least squares, linear regression, or multi-linear regression methods. This step requires recording a first set of unweighted rib-cage sensor readings (RC) and abdominal sensor readings (AB) for each breath at a first position and first breathing pattern of the subject. The volume of the tidal flow of breathing is also simultaneously recorded by the airway monitoring device 22. After the data is recorded, the least squares technique may be used to determine the scaling factor K for the rib-cage and abdomen contributions to the tidal volume. The scaling factor K may then be used to determine the multiplicative value M, using the following equation:

$$M=V/(K(RC)+(AB)),$$

where V is the average volume measured for each breath by the airway monitoring device 22.

The above may then be repeated for at least one other position or breathing pattern of the subject which affects the contributions of rib-cage and abdomen to the tidal volume (i.e., has a different scaling factor) and the values of the scaling factors K and the multiplicative values of each set of readings may then be averaged.

Instead of the using the least squares to determine the scaling factor K and multiplicative value M for each point, linear regression or multi-linear regression may be used to draw a line connecting the average points of each set of measurements to determine the scaling factor. The resulting scaling factor may then be used to determine the multiplicative value M using the above equation.

The above described procedures produce an optimal multiplicative value M at the expense of a less accurate estimation, i.e., average, of the scaling factor $K_A$ of rib-cage and abdomen contributions. At least one of the scaling amplifiers 16, 18 is adjusted to implement the calculated value of the scaling factor $K_A$ and/or the multiplicative value. This step uses least squares, linear regression, or multi-linear regression techniques over a single breath or from trough to peak of a single breath during one or two postures and with or without voluntarily changing the thoracoabdominal contributions to tidal volume as described in U.S. Pat. No. 4,373,534. Changing of rib-cage and abdomen contributions to tidal volume during this step between each set of readings may be accomplished by a) voluntary breathing maneuvers, b) postural alterations, for example, supine to semirecumbent or c) breathing freely for one set of rib-cage and abdomen contributions to tidal volume, then cinching the rib-cage or abdomen with a surgical abdominal binder to obtain other sets.

After performing step 100, a current scaling factor K is then computed using the Qualitative Device Calibration (QDC) procedure as described in U.S. Pat. No. 4,834,109, step 110. This step involves recording rib-cage and abdomen signals for a steady state baseline period. Next, the standard deviations or average variability of rib-cage and abdomen signals are calculated. The ratio of the standard deviations or average variability of the rib cage to the abdomen readings are used to determine the current scaling factor $K_C$ as follows:

$$K_C=SD(AB)/SD(RC),$$

wherein,

SD(AB) is the standard deviation or average variability of the abdomen readings; and SD(RC) is the standard deviation or average variability of the rib-cage readings.

Step 110 may comprise computing the current scaling factor $K_C$ at regular periodic intervals throughout the monitoring period to ensure that the current scaling factor $K_C$ is being used. This step is important because a change in posture typically accompanies a change in the relative contributions of the rib-cage and the abdomen to the tidal volume of breaths. Accordingly, the posture of the subject may be monitored via, for example, an accelerometer mounted on the subject's back so that the current scaling factor $K_C$ may be computed when a change in the subject's posture is detected. Furthermore, the frequency of the breathing pattern may also affect the relative contributions of the rib-cage and abdomen signals on the tidal volume. Therefore, the breathing patterns may additionally or alternatively be monitored so that the current scaling factor $K_C$ is computed when a change in the breathing pattern is detected which may affect the relative contributions of the rib-cage and abdomen to the tidal volume.

After step 110, the current scaling factor $K_C$ computed using the QDC method in step 110 is used to accurately diagnose obstructive apneas since it is based on the present conditions and the multiplicative M computed using one of the least squares, linear regression, and multi-linear regression in step 100 is used together to provide a better estimate of actual tidal volume during various postures and breathing patterns of the subject.

In a further embodiment, the QDC method may be used to determine an initial scaling factor $K_I$, before the step of determining the multiplicative value M using least squares, linear regression, or multi-linear regression techniques. Instead of performing step 110, the initial scaling factor $K_I$, may be used in step 120, for example, if the subject has not changed breathing patterns or posture. However, step 110 is performed and the current scaling factor $K_C$ is used in step 120 in the preferred embodiments.

The spirometer or other airway monitoring device may be used during the monitoring period to measure the tidal volume while the tidal volume is also computed using the current scaling factor $K_C$ values which are periodically computed using the QDC procedure and the optimal M value computed using the least squares, linear regression, or multi-linear regression. The calculated tidal volume value may be compared to the measured tidal volume to assess the effectiveness of the non-invasive ventilatory device. Furthermore, the controller may be operatively arranged to set off an alarm when the difference between the measured tidal volume and the calculated tidal volume is greater than an alarm value. Instead of alarming, the controller may attempt to tighten the mask of the airway monitoring device to alleviate the discrepancy before activating the alarm.

While there have been shown and described and pointed out fundamental novel features of the present invention as applied to a preferred embodiment thereof, it will be understood that various omissions and substitutions and changes in the methods described and in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A method for calibrating a non-invasive breathing monitor having a rib-cage sensor and an abdomen sensor for diagnosing obstructive apneas and providing an estimation of tidal volume, comprising the steps of:

(a) determining a multiplicative factor (M) for use with readings from the rib cage sensor and the abdominal sensor for estimating tidal volume by a method including the steps of:
   (i) recording a first set of readings from the rib cage sensor (RC) and the abdomen sensor (AB), and a tidal flow volume (V) as measured by an airway monitoring device while recording the first set of readings;
   (ii) determining a first scaling factor ($K_I$) for relative contributions of said rib cage sensor and said abdomen sensor to said tidal volume using one of the least squares, linear regression, and multi-linear regression techniques applied to the first set of readings;
   (iii) applying the first scaling factor to said first set of readings to obtain, $K_I(RC)+(AB)$, the first scaled set of readings; and
   (iv) calculating the multiplicative factor (M) by dividing the tidal volume reading (V) by the first scaled set of readings using the equation:

$$M=V/(K_1(RC)+(AB)),$$

and (b) determining a current scaling factor for the current posture and breathing pattern of the subject for use with readings from the rib-cage sensor and abdomen sensor for diagnosing apneas by recording a current set of readings from the rib cage sensor and the abdomen sensor, determining a standard deviation of each of these recordings, and setting the current scaling factor equal to a ratio of the standard deviations.

2. The method of claim 1, wherein said recording a current set of readings comprises recording for a baseline period at a substantially steady state tidal volume, wherein said determining a standard deviation comprises calculating one of a standard deviation and an average variability of each of said rib-cage and abdomen readings during the baseline period, and wherein said setting comprises calculating the current scaling factor in accordance with the equation:

$$K_C=SD(AB)/SD(RC),$$

wherein: $K_C$=the current scaling factor, SD(AB)=the one of the standard deviation and the average variability of the abdomen readings, and SD(RC)=the one of the standard deviation and the average variability of the rib-cage readings.

3. A method for calibrating a non-invasive breathing monitor having a rib-cage sensor and an abdomen sensor for diagnosing obstructive apneas and providing an estimation of tidal volume, comprising the steps of:

(a) determining a multiplicative factor (M) for use with readings from the rib cage sensor and the abdominal sensor for estimating tidal volume by a method including the steps of:
   (i) recording a first set of readings from the rib cage sensor and the abdomen sensor; recording a second set of readings from the rib cage sensor and the abdomen sensor having a different scaling factor than said first set of readings; and recording the tidal volume (V) as measured by an airway monitoring device while recording the first and second sets of readings;
   (ii) determining a first scaling factor ($K_I$) for relative contributions of said rib cage sensor and said abdomen sensor to said tidal volume using one of the least squares, linear regression, and multi-linear regression techniques applied to the first and second sets of readings;
   (iii) applying the first scaling factor to said first and second set of readings to obtain, $K_I(RC)+(AB)$, the first scaled set of readings, wherein: AB=the average of unweighted abdomen sensor readings in the first and second sets; and RC=the average of the unweighted rib-cage sensor readings in the first and second sets; and
   (iv) calculating the multiplicative factor (M) by dividing the tidal volume reading (V) by the first scaled set of readings using the equation:

$$M=V/(K_1(RC)+(AB)),$$

and (b) determining a current scaling factor for the current posture and breathing pattern of the subject for use with readings from the rib-cage sensor and abdomen sensor for diagnosing apneas by recording a current set of readings from the rib cage sensor, determining a standard deviation of each of these recordings, and setting the current scaling factor equal to a ratio of the standard deviations.

4. The method of claim 3, wherein said recording a current set of readings comprises recording rib-cage and abdomen readings from the abdomen and rib cage sensors for a baseline period at a substantially steady state tidal volume, wherein said determining a standard deviation comprises calculating one of a standard deviation and an average variability of each of said rib-cage and abdomen readings during the baseline period; and wherein said setting comprises calculating the current scaling factor in accordance with the equation:

$$K_C = SD(AB)/SD(RC)$$

wherein: $K_C$=current scaling factor, SD(AB)=the one of the standard deviation and the average variability of the abdomen readings; and SD(RC)=the one of the standard deviation and the average variability of the rib-cage readings.

5. A method for calibrating a non-invasive breathing monitor having a rib-cage sensor and an abdomen sensor for diagnosing obstructive apneas and providing an estimation of tidal volume, comprising the steps of:

(a) determining a multiplicative value for use with readings from the rib cage sensor and abdomen sensor for estimating tidal volume by simultaneously recording a first set of readings from the rib cage sensor and the abdomen sensor and a tidal volume reading using an airway monitoring device, determining an average scaling factor for relative contributions of said rib cage sensor and said abdomen sensor to said tidal volume via one of at least square, linear regression, and multi-linear regression techniques, applying the average scaling factor to said first set of readings to obtain a first scaled set of readings, and calculating the multiplicative value by dividing the tidal volume reading by the first scaled set of readings; and (b) determining a current scaling factor ($K_C$) for the current posture and breathing pattern of the subject for use with readings from the rib-cage sensor and abdomen sensor for diagnosing apneas by:

(i) recording rib-cage and abdomen readings from the abdomen and rib cage sensors for a baseline period at a substantially steady state tidal volume;

(ii) calculating one of a standard deviation and an average variability of each of said rib-cage abdomen readings during the baseline period; and (iii) calculating the current scaling factor in accordance with the equation:

$$K_C = SD(AB)/SD(RC)$$

wherein: SD(AB)=the one of the standard deviation and the average variability of the abdomen readings; and SD(RC)= the one of the standard deviation and the average variability of the rib-cage readings.

* * * * *